(12) United States Patent
Gerlitz

(10) Patent No.: US 11,260,240 B2
(45) Date of Patent: Mar. 1, 2022

(54) APPARATUS ATTACHABLE TO A LOW-LEVEL LASER THERAPY DEVICE TO TRANSMIT LIGHT OR INFRARED LIGHT THROUGH THE FUR OF AN ANIMAL ONTO THE ANIMAL'S SKIN

(71) Applicant: Yonatan Gerlitz, Lev Hasharon (IL)

(72) Inventor: Yonatan Gerlitz, Lev Hasharon (IL)

( * ) Notice: Subject to any disclaimer, the term of this patent is extended or adjusted under 35 U.S.C. 154(b) by 78 days.

(21) Appl. No.: 16/423,769

(22) Filed: May 28, 2019

(65) Prior Publication Data
US 2019/0366116 A1    Dec. 5, 2019

Related U.S. Application Data

(60) Provisional application No. 62/678,100, filed on May 30, 2018.

(51) Int. Cl.
*A61N 5/00* (2006.01)
*A61N 5/06* (2006.01)
*A61D 99/00* (2006.01)
*A61N 5/067* (2006.01)

(52) U.S. Cl.
CPC ........... *A61N 5/0616* (2013.01); *A61D 99/00* (2013.01); *A61N 5/067* (2021.08); *A61N 2005/063* (2013.01); *A61N 2005/0632* (2013.01); *A61N 2005/0644* (2013.01); *A61N 2005/0659* (2013.01); *A61N 2005/0662* (2013.01); *A61N 2005/0664* (2013.01)

(58) Field of Classification Search
USPC ......................................................... 607/79
See application file for complete search history.

(56) References Cited

U.S. PATENT DOCUMENTS

| | | | | |
|---|---|---|---|---|
| 5,300,097 A | * | 4/1994 | Lerner ................. | A61N 5/0617 607/93 |
| 5,803,093 A | * | 9/1998 | Romano ................ | A45D 24/22 132/114 |
| 6,053,180 A | * | 4/2000 | Kwan .................... | A01K 13/00 132/118 |
| 6,497,719 B2 | * | 12/2002 | Pearl .................... | A61N 5/0617 607/89 |
| 7,194,316 B2 | * | 3/2007 | Bousfield ............... | A61N 1/322 433/29 |
| 8,518,029 B2 | * | 8/2013 | Birmingham ........ | A61N 5/0617 606/9 |
| 8,771,327 B2 | * | 7/2014 | Pearl .................... | A61N 5/0617 607/90 |
| D756,527 S | * | 5/2016 | Cole ........................... | D24/200 |
| 9,561,386 B2 | * | 2/2017 | Pearl .................... | A61N 5/0617 |
| 2002/0077679 A1 | * | 6/2002 | Lo ........................ | A61N 5/0617 607/90 |

(Continued)

OTHER PUBLICATIONS

Israel Patent Office (as ISA), "International Search Report" (Form PCT/ISA/210), PCT Patent Application No. PCT/IB2019/054442; dated Oct. 10, 2019; pp. 1-3.

(Continued)

*Primary Examiner* — Shirley X Jian
(74) *Attorney, Agent, or Firm* — Rod D. Baker

(57) ABSTRACT

An attachment apparatus for use in combination with a known low-level laser therapy device. The apparatus is attachable to the front portion of, and operable with, a low-level laser therapy device for passing coherent light past the fur of an animal patient. The apparatus has a body with a plurality of pins that can be pushed through the fur, and which transmit a low-level laser therapy light to skin of the animal. The pins are composed of material that transmits the required light wavelength to the animal's skin.

8 Claims, 2 Drawing Sheets

(56) References Cited

U.S. PATENT DOCUMENTS

| | | | | |
|---|---|---|---|---|
| 2002/0128696 | A1* | 9/2002 | Pearl | A61N 5/0617 |
| | | | | 607/89 |
| 2005/0251242 | A1* | 11/2005 | Bousfield | A61N 5/0617 |
| | | | | 607/150 |
| 2007/0149900 | A1* | 6/2007 | Lin | A61H 7/006 |
| | | | | 601/15 |
| 2007/0179573 | A1* | 8/2007 | Laurent | A61N 5/0617 |
| | | | | 607/89 |
| 2008/0125835 | A1* | 5/2008 | Laurent | A61N 5/0617 |
| | | | | 607/89 |
| 2008/0172113 | A1* | 7/2008 | Gourgouliatos | A61N 5/0617 |
| | | | | 607/90 |
| 2008/0172115 | A1* | 7/2008 | Gourgouliatos | A61N 5/0617 |
| | | | | 607/94 |
| 2008/0215123 | A1* | 9/2008 | Maricle | A01K 13/002 |
| | | | | 607/89 |
| 2009/0270845 | A1* | 10/2009 | Birmingham | A61N 5/0617 |
| | | | | 606/2 |
| 2012/0123305 | A1* | 5/2012 | Pearl | A45D 24/00 |
| | | | | 601/15 |
| 2014/0338211 | A1* | 11/2014 | Kaizuka | A45D 20/122 |
| | | | | 34/97 |
| 2019/0126061 | A1* | 5/2019 | Hong | A61N 5/0617 |

OTHER PUBLICATIONS

Israel Patent Office (as ISA), "Written Opinion of the International Searching Authority" (Form PCT/ISA/237) PCT Patent Application No. PCT/IB2019/054442; dated Oct. 10, 2019; pp. 1-4.

* cited by examiner

APPARATUS ATTACHABLE TO A LOW-LEVEL LASER THERAPY DEVICE TO TRANSMIT LIGHT OR INFRARED LIGHT THROUGH THE FUR OF AN ANIMAL ONTO THE ANIMAL'S SKIN

CROSS-REFERENCE TO RELATED APPLICATIONS

This application claims the benefit of the filing of U.S. Provisional Patent Application Ser. No. 62/678,100 titled "Apparatus Attachable to a Low-Level Laser Therapy Device to Transmit Light or Infrared Light Through the Fur of an Animal Onto the Animal's Skin," filed on 30 May 2018, the specification of which is incorporated herein by reference.

BACKGROUND OF THE INVENTION

Field of the Invention

The invention relates to low-level laser therapy, particularly to low-level laser therapy devices for use with animals, and specifically to an attachment apparatus for use with low-level laser therapy devices intended for treating furred animals.

BACKGROUND OF THE INVENTION

In recent years, low-level laser therapy (LLLT) devices have been proven successful in promoting the healing of various problems in humans and animals. There is, however, an unsolved problem in treating, with LLLT, furry animal patients due to the fur's strong absorption and scattering of the therapeutic light. The current solution to this problem is the shaving of the fur in the treatment area, prior to treatment.

SUMMARY OF THE INVENTION

There is disclosed an apparatus that is configured similarly to a hairbrush—but the apparatus is not a hairbrush. The apparatus is an attachment for use with a low-level laser therapy device. The apparatus is attachable to the front portion of, and operatively engageable with, a low-level laser therapy device, for passing coherent light and infrared light past the fur of an animal. The apparatus has a body with a plurality of columns or "pins" that are pushable through the fur, and which transmit a coherent low-level laser therapy light to the animal's skin. The plurality of pins can be readily pushed through the fur, and are composed of material that transmits the required light wavelength from the LLLT device to the animal's skin. The apparatus is configured to maintain properties of coherence of the light in each area.

BRIEF DESCRIPTION OF THE DRAWING

The accompanying drawings, which are incorporated into and form a part of the specification, illustrate one embodiment of the present invention and, together with the description, serve to explain the principles of the invention. The drawings are only for the purpose of illustrating a preferred embodiment of the invention and are not to be construed as limiting the invention. In the drawings.

DISCLOSURE OF A PREFERRED EMBODIMENT

Figure 1:
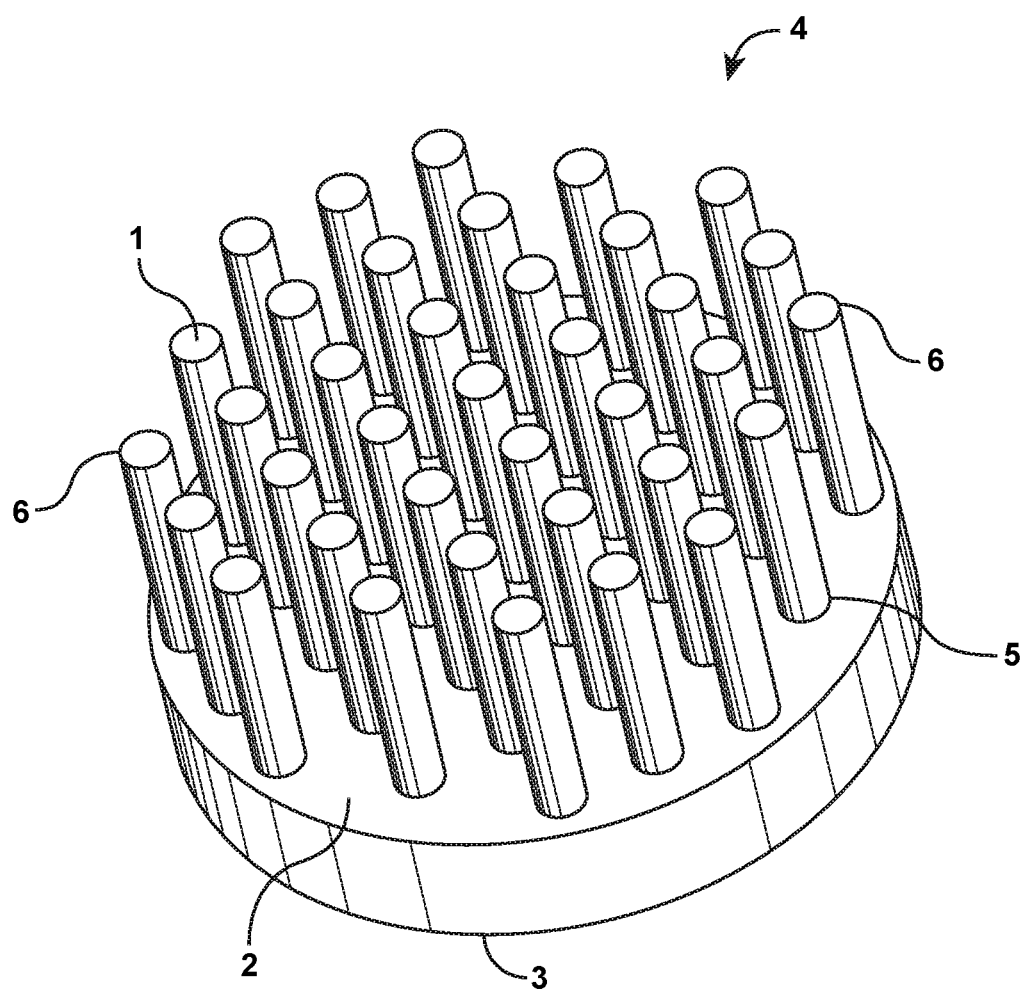
FIG. 1 is a perspective front view of an apparatus according to the present invention, which is operatively attachable to the front of a low-level laser therapy device of known type and operation.

FIG. 1 is a three-dimensional illustration of the present apparatus 4 to be attached to the front of a low-level laser therapy (LLLT) device (device not shown in FIG. 1). The apparatus 4 is adapted to be removably attachable to any of several of the LLLT devices known in the industry. Such attachment may be of any suitable means, such as with resilient clips or the like. When the apparatus 4 is attached to an LLLT device, collimated light energy is transmitted from the LLLT device to the apparatus 4, and then via the apparatus 4 toward the animal patient's skin.

The apparatus has a back surface 3, a front surface 2 and a plurality of transmitting pins 1. The apparatus 4 may be, but is not necessarily, unitary, as by fabrication by molding as an integral unit. The apparatus 4 may be composed, for example, of polycarbonate or poly(methyl methacrylate). The front surface 2 is generally planar and is highly polished. The back surface 3 likewise is planar and highly polished. A plurality of transmitting pins 1 extend from the front surface 2 of the apparatus 4. As seen in FIG. 1, the pins 1 preferably are arranged in rows, there being seven rows of pins seen in FIG. 1 (by way of example). The array of pins may have the pins in adjacent rows relatively staggered, or arranged in offset columns, so to increase the efficient transmission of therapy light to an area of the veterinary patient's skin. In one preferred embodiment, the pins 1 have axial lengths (extending from the front surface 2 of the body of the apparatus 4) within the range of from about 10 millimeters (mm) to about 20 millimeters. The pins 1 preferably, but not necessarily, are approximately equal in axial length, as extended from the front surface 2. Each pin 1 preferably, but not by way of critical limitation, is cylindrical in lateral cross-section, with a diameter of between about 1.0 millimeter and about 2.0 millimeter.

Each pin 1 has a free front end whose surface 6 preferably is generally planar as seen in the drawing figures. The pin front end surfaces 6 are polished to improve the emission of collimated therapy light. The proximate ends 5 of the pins 1 are where the pins juncture with the body of the apparatus 4. The back surface 3, the front surface 2 and the front end surfaces 6 of the pins 1 are mutually parallel and polished, so that coherent light that enters the back surface 3 (from the LLLT device 10, FIG. 2) and then emerges as a coherent light beam from the front end surface 6 of each pin 1. The distances between pins 1 should be minimal, preferably with no more than about 0.5 mm separating the front ends 6, except that the pins 1 are sufficiently separated so to allow the pins to pass through the animal's fur when the apparatus 4 is gently pressed down through the fur to the animal's skin.

Figure 2:
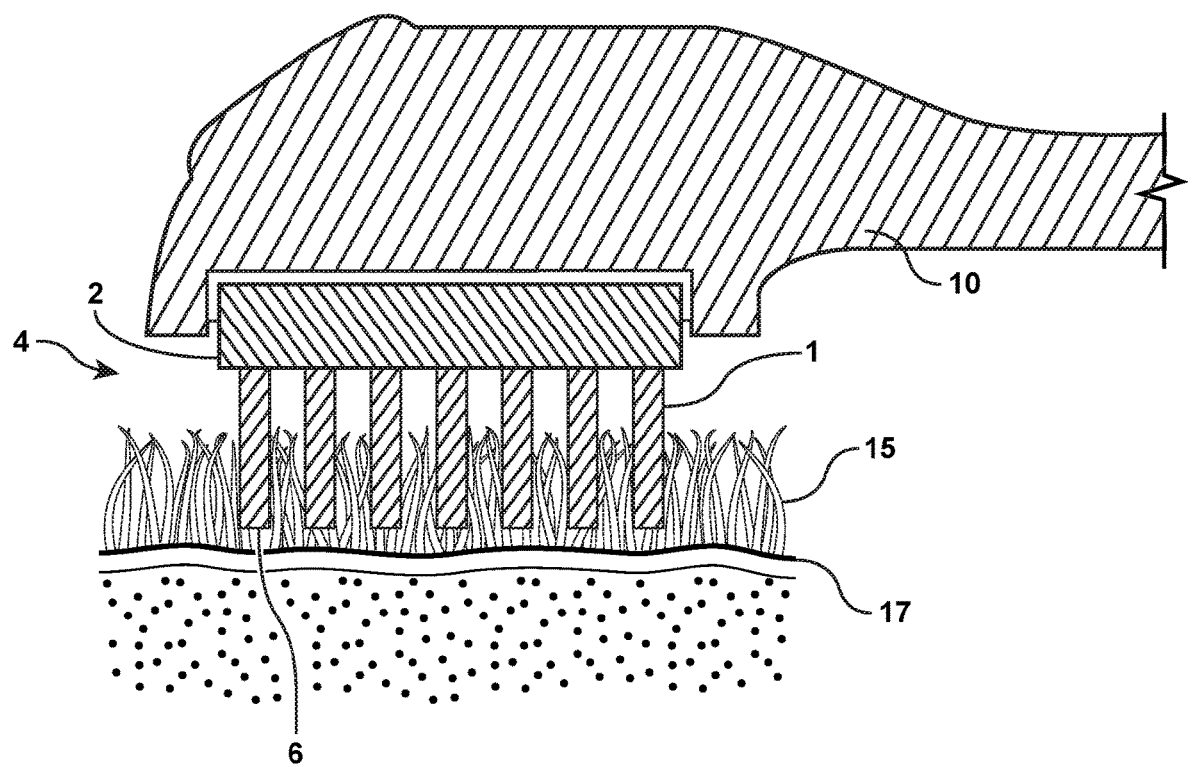
FIG. 2 is a side sectional view of the apparatus according to the present invention, shown engaged with the front of a low-level laser therapy device, and with the pins of the apparatus penetrated through an animal's fur to dispose the apparatus pins adjacent the animal's skin.

Combined reference is made to FIGS. 1 and 2. In the practice of the invention to treat a furred animal, such as livestock or a pet, the apparatus 4 is attached (e.g., removably attached) to a known LLLT appliance or device 10, such that coherent light emitted from the LLLT device 10 enters the apparatus 4 via the back surface 3. Consequently, the coherent light passes through the body of the apparatus 4 and into the transmitting pins 1. Coherent light thus transmitted through the apparatus 4 is then emitted from the front end surfaces 6 of the pins 1, and toward the animal to be treated. The transmitting pins 1 thus are pushed through the animal's fur 15 to locate the end surfaces 6 near the skin 17, so the coherent light can be applied directly to the animal's skin.

The front surface 2 is preferably polished and parallel to back surface 3, so that it can pass additional coherent light to the animal's skin 17. But light passing through the surface 2 (and not through the pins 1) must pass through the fur 15, so efficiency is reduced therefor.

Similar devices can be applied also for non-coherent light. For non-coherent light, an apparatus which collects more energy, and which passes through the fur, and which will transmit more light power but will lose part of the coherence, can be designed.

Although the invention has been described in detail with particular reference to these preferred embodiments, other embodiments may achieve the same results. In the previous description, specific details are set forth, such as specific materials, structures, chemicals, processes, etc., in order to provide a thorough understanding of the present invention. However, as one having ordinary skill in the art would recognize, the present invention can be practiced without resorting to the details specifically set forth. In other instances, well known principles of mechanics and physics have not been described in detail, in order not to unnecessarily obscure the present invention.

Only some embodiments of the invention and but a few examples of its versatility are described in the present disclosure. It is understood that the invention is capable of use in various other combinations and is capable of changes or modifications within the scope of the inventive concept as expressed herein. Modifications of the invention will be obvious to those skilled in the art and it is intended to cover with the appended claims all such modifications and equivalents.

What is claimed is:

1. An apparatus, attachable to the front of a low-level laser therapy device, for passing coherent therapy light past a fur of an animal, the apparatus comprising:

a planar polished back surface disposable at the front of the low-level laser therapy device;

a plurality of solid pins pushable through the fur and for transmitting coherent therapy light to a skin of the animal, each pin having a planar front end surface for passing collimated therapy light toward a skin of the animal;

a polished planar front surface for passing additional coherent therapy light toward the skin;

the planar front end surfaces of the pins, and the planar front surface, being parallel to the planar back surface; and coherent therapy light from the low-level laser therapy device enters the back surface, is transmitted via a solid material comprising the pins, and emerges as a coherent light beam from the front end surfaces of the pins.

2. The apparatus of claim 1 wherein the coherent therapy light from the low-level laser therapy device enters the back surface, and emerges from the polished planar front surface.

3. The apparatus of claim 1 wherein a distance between pins is equal to or less than 0.5 mm.

4. The apparatus of claim 1 wherein the solid material of the pins comprises polycarbonate or poly(methyl methacrylate).

5. An apparatus, attachable to the front of a low-level laser therapy device, the apparatus comprising a plurality of pins, each pin consisting of a solid material, pushable through fur, and for transmitting low-level coherent laser therapy light to a skin of an animal, and therapy light from the laser therapy device enters a planar polished back surface of the apparatus and is transmitted via the solid material of the pins to emerge as a coherent light beam from a planar front end surface of each pin.

6. The apparatus of claim 5 wherein the apparatus comprises a unit integrally molded of polycarbonate or poly(methyl methacrylate).

7. The apparatus of claim 5 wherein the planar front end surface of each pin is parallel to the planar polished back surface.

8. The apparatus of claim 6 wherein the unit further comprises a polished front surface from which the pins extend, and therapy light from the laser therapy device enters the planar polished back surface of and emerges from the polished front surface.

\* \* \* \* \*